(12) United States Patent
Hausslein et al.

(10) Patent No.: US 6,287,484 B1
(45) Date of Patent: Sep. 11, 2001

(54) IONTOPHORETIC MATERIAL

(76) Inventors: Robert Hausslein, 20 Slocum Rd., Lexington, MA (US) 02173; Fredric Milder, 204 Clinton Rd., Brookline, MA (US) 02445; Anne Marie Cromwick, 11 Donna Rd., Saugus, MA (US) 01906; Meir Rosenberg, 27 Burdean Rd., Newton, MA (US) 02159; Stephen Keaney, 476 Townsend Rd., Groton, MA (US) 01450

( * ) Notice: Subject to any disclaimer, the term of this patent is extended or adjusted under 35 U.S.C. 154(b) by 0 days.

(21) Appl. No.: 09/288,606

(22) Filed: Apr. 8, 1999

Related U.S. Application Data

(63) Continuation-in-part of application No. 09/037,156, filed on Mar. 9, 1998, now Pat. No. 6,060,000, which is a continuation-in-part of application No. 08/613,157, filed on Mar. 8, 1996, now Pat. No. 5,725,817, which is a continuation of application No. 08/212,157, filed on Mar. 14, 1994, now Pat. No. 5,498,248, which is a division of application No. 07/975,597, filed on Nov. 12, 1992, now Pat. No. 5,322,520.

(51) Int. Cl.⁷ .............................. H01B 1/22; A61M 25/00; A61M 39/00
(52) U.S. Cl. ................... 252/512; 252/514; 604/93; 604/265; 424/618; 424/630
(58) Field of Search ................ 252/503, 512, 252/513, 514; 428/407; 424/618, 630; 604/93, 265

(56) References Cited

U.S. PATENT DOCUMENTS

| | | |
|---|---|---|
| 486,902 | 11/1892 | Shults . |
| 2,276,623 | 3/1942 | Meiman ............................ 32/15 |
| 2,355,231 | 8/1944 | Moore ......................... 128/172.1 |
| 3,659,588 | 5/1972 | Kahn et al. .................... 128/2 R |
| 3,848,603 | 11/1974 | Throner ..................... 128/349 R |
| 3,964,477 | 6/1976 | Ellis et al. .................... 128/172.1 |
| 3,970,530 | 7/1976 | Maslowski et al. ............ 426/237 |
| 4,027,393 | 6/1977 | Ellis et al. ........................ 32/10 A |
| 4,054,139 | 10/1977 | Crossley ........................ 128/260 |
| 4,105,732 | 8/1978 | Slingluff ........................ 264/104 |
| 4,126,937 | 11/1978 | Ellis et al. ........................ 32/15 |
| 4,209,480 | 6/1980 | Homsy .......................... 264/108 |
| 4,252,525 | 2/1981 | Child ............................. 433/173 |
| 4,253,463 | 3/1981 | Kim .............................. 128/348 |
| 4,291,125 | 9/1981 | Greatbatch .................... 435/240 |
| 4,292,968 | 10/1981 | Ellis ........................... 128/207.21 |
| 4,308,859 | 1/1982 | Child ............................. 128/1 R |
| 4,313,438 | 2/1982 | Greatbatch ................. 128/207.21 |
| 4,374,186 | 2/1983 | McCartney et al. ............ 429/154 |
| 4,411,648 | 10/1983 | Davis et al. ..................... 604/21 |
| 4,419,091 | 12/1983 | Behl et al. ....................... 604/20 |
| 4,474,570 | 10/1984 | Ariura et al. .................... 604/20 |

(List continued on next page.)

FOREIGN PATENT DOCUMENTS

| | | | |
|---|---|---|---|
| 3830359 | 12/1989 | (DE) | ........................ A61M/25/00 |
| 0206024 | 12/1986 | (EP) | ........................ A61L/29/00 |
| 1582016 | 12/1980 | (GB) | ........................ A61M/25/00 |
| WO9116946 | 11/1991 | (WO) | ........................ A61N/1/30 |
| 98/20331 | * 5/1998 | (WO) . | |

OTHER PUBLICATIONS

J.A. Spadaro et al., "Antibacterial Effects of Silver Electrodes with Weak Direct Current", *Antimicrobial Agents and Chemotherapy*, vol. 6, No. 5, Nov. 1974, pp. 637–642.

C. R. Davis et al., "Electrode and Bacterial Survival with Iontophoresis in Synthetic Urine", *The Journal of Urology*, vol. 147, May 1992, pp. 1310–1313.

*Primary Examiner*—Mark Kopec
(74) *Attorney, Agent, or Firm*—Gunster, Yoakley & Stewart, P.A.

(57) ABSTRACT

A material is provided that uses controlled electrical current derived from dissimilar galvanic materials to drive oligodynamic metal ions into solution.

10 Claims, 6 Drawing Sheets

U.S. PATENT DOCUMENTS

| | | | |
|---|---|---|---|
| 4,476,590 | 10/1984 | Scales et al. | 3/1.91 |
| 4,483,688 | 11/1984 | Akiyama | 604/265 |
| 4,525,253 | 6/1985 | Hayes et al. | 204/149 |
| 4,539,234 | 9/1985 | Sakamoto et al. | 427/393.5 |
| 4,564,361 | 1/1986 | Akiyama | 604/265 |
| 4,569,673 | 2/1986 | Tesi | 604/20 |
| 4,581,028 | 4/1986 | Fox, Jr. et al. | 623/2 |
| 4,603,152 | 7/1986 | Laurin et al. | 604/265 |
| 4,607,623 | 8/1986 | Bauman | 128/11 |
| 4,609,508 | 9/1986 | Edeling et al. | 264/29.6 |
| 4,642,104 | 2/1987 | Sakamoto et al. | 604/264 |
| 4,722,344 | 2/1988 | Cambron et al. | 128/658 |
| 4,814,307 | 3/1989 | Funabashi et al. | 502/101 |
| 4,817,594 | 4/1989 | Juhasz | 128/155 |
| 4,886,075 | 12/1989 | Jones | 128/787 |
| 4,886,505 | 12/1989 | Haynes et al. | 604/265 |
| 4,915,685 | 4/1990 | Petelenz et al. | 604/20 |
| 4,973,320 | 11/1990 | Brenner et al. | 604/265 |
| 5,037,395 | 8/1991 | Spencer | 604/113 |
| 5,049,140 | 9/1991 | Brenner et al. | 604/266 |
| 5,057,072 | 10/1991 | Phipps | 604/20 |
| 5,084,006 | 1/1992 | Lew et al. | 604/20 |
| 5,151,222 | 9/1992 | Ruffoni | 252/511 |
| 5,154,165 | 10/1992 | Elliott et al. | 128/419 R |
| 5,302,172 | 4/1994 | Sage, Jr. et al. | 604/20 |
| 5,322,520 | 6/1994 | Milder | 604/265 |
| 5,324,275 | 6/1994 | Raad et al. | 604/265 |
| 5,328,451 | 7/1994 | Davis et al. | 604/20 |
| 5,421,982 | 6/1995 | Ikeda et al. | 204/414 |
| 5,544,098 | 8/1996 | Myers et al. | 264/104 |
| 5,549,849 | 8/1996 | Namura et al. | 252/503 |
| 5,607,691 | 3/1997 | Hale et al. | 424/449 |
| 5,725,817 | 3/1998 | Milder | 264/104 |
| 5,741,224 | 4/1998 | Milder et al. | 604/20 |
| 5,759,564 | 6/1998 | Milder et al. | 424/426 |
| 6,042,751 * | 3/2000 | Chan et al. | 252/511 |

* cited by examiner

IONTOPHORETIC MATERIAL

CROSS REFERENCE TO RELATED APPLICATIONS

This application is a continuation-in-part of U.S. patent application Ser. No. 09/037,156, filed Mar. 9, 1998 now U.S. Pat. No. 6,060,000, which is a continuation-in-part of U.S. patent application Ser. No. 08/613,157, filed Mar. 8, 1996 and issued as U.S. Pat. No. 5,725,817, which is a continuation of U.S. patent application Ser. No. 08/212,157, filed Mar. 14, 1994 and issued as U.S. Pat. No. 5,498,248, which is a divisional of U.S. patent application Ser. No. 07/975,597, filed Nov. 12, 1992 and issued as U.S. Pat. No. 5,322,520.

STATEMENT REGARDING FEDERALLY-SPONSORED RESEARCH

Not Applicable.

1. Field of the Invention

The invention relates to oligodynamic iontophoresis, and more particularly to a structure for medical devices that reduces or eliminates infection by killing microorganisms with controlled iontophoresis.

2. Background of the Invention

Oligodynamic metals, such as silver, are effective in minute quantities as bacteriostats and bactericides. The most active form of these oligodynamic metals is as ions in solution. While the precise nature of the bactericidal effect is unknown, it is believed to involve altering the function of the cell membrane or linking to the cell's DNA to disrupt cell function. The bactericidal action is effective against a broad spectrum of bacteria, including all of the common strains which cause infection. When these metals are used in the minute concentrations required to kill or stem the growth of bacteria, they do not have any detrimental effect on normal mammalian cells.

Silver is used routinely in antibacterial salves, such as silver sulfadiazine, and has also been used in clinical trials to coat gauze for burn dressings. Medical devices, such as catheters, with silver impregnated in a soluble collagern or polymer coating are also known. After these catheters are placed, the coating slowly dissolves and the silver is released over time into the environment. The infection rates with these products are reported to be two to four times lower than standard catheters.

One catheter that uses silver as an antibacterial agent has had only limited success because the device, consisting of a silver impregnated collagen cuff which is inserted just below the skin, is difficult to place correctly. The cuff is also expensive, increasing the cost of a central venous catheter almost three-fold. Other catheters for reducing infection rates use well known approaches, most of them varying only in the type and solubility of the silver or silver-alloy coating.

Many of the prior art catheters that use oligodynamic metals as bacteriostats fail to adequately prevent infection for one or more of the following reasons: 1) Silver released from soluble coatings, is not always in the same charge state and often is not charged at all, therefore its bactericidal potential is not optimized; 2) With soluble-coated catheters, once the coating dissolves, usually over about two weeks there is no further antibacterial protection; 3) A non-soluble silver, silver alloy or silver-oxide coating can prevent colonization of the catheter to a limited extent, but the oligodynamic metal is not released into the surrounding fluid or tissue; 4) Due to the substantial change in the catheter placement procedure, the use of these catheters requires additional personnel training; and 5) Although infection can enter the body through either the interior or the exterior of the catheter, not all catheters provide both interior and exterior protection. Furthermore, despite the capability of silver-alloy coated devices to produce a two to four fold reduction in bacterial colonization, their high cost greatly detracts from their modest capabilities.

Research from the 1970's onward has been directed toward improving the antibacterial effects of oligodynamic metals by electrically injecting the metal ions into solution. This process, known as oligodynamic iontophoresis, is capable of reducing bacterial colonization fifteen to one-hundred fold. Iontophoresis describes the movement of ions in a conductive fluid under the influence of low-strength electric fields, and in this context refers to the forcing of ions into a conductive fluid environment using minute electric currents. For example, if two electrodes made of a metal, such as silver, are introduced into a conductive medium, such as saline, blood or urine, and an electrical potential is applied across the electrodes, silver ions are driven into solution creating an enhanced bactericidal effect. The current required to safely drive a sufficient amount of silver ions into solution to control infection is in the range of 1 to 400 microAmperes. This current range does not cause localized cell necrosis and it is below the sensory or pain threshold.

Despite its great potential, the oligodynamic iontophoresis phenomenon has found limited use in conjunction with medical devices, although urological or Foley catheters have progressed to animal experiments. With respect to Foley catheters, researchers have identified several deficiencies in prior art devices. Foremost is that the electrodes used to force ions into solution wear out, or corrode, at the interface between air and the conductive medium. This problem probably also arises in blood or saline environments as well as urine. Other significant drawbacks with prior art iontophoretic devices include bulky, current controlled power sources required for driving the electrodes; electrode configurations that do not protect both the outside and the inside of the catheter; and manufacturing processes that are labor intensive.

An example of an infection control catheter that uses separate electrodes on the catheter and an external power supply to drive ions into solution is U.S. Pat. No. 4,411,648 to Davis. Other prior art oligodynamic iontophoresis devices do not use external power supplies. For example, U.S. Pat. No. 4,886,505 to Haynes, teaches placing two metals in direct physical contact to produce electrical currents. The currents produced, however, are likely to be too large to be safely used and possibly will alter the pH of the environment. In German Patent Document DE 3,830,359, two dissimilar metal powders not in electrical contact with each other are embedded in a nonconductive catheter material, such as electrically insulating polymers. Because of the separation of dissimilar metals by an insulator, it is not likely that there is any iontophoresis effect in this device as a result of a potential being created by the dissimilar metals, except for the possibility of when a biofilm forms on the catheter surface to complete the circuit. Were an electrical circuit to be formed in this manner, the current density would not be regulated or predictable, and the current produced therefore could be either too high to be safe or too low to be effective.

An oligodynamic iontophoresis catheter which uses the properties of metals to generate a current and to form an ion barrier for killing bacteria at a localized body entry is disclosed in U.S. Pat. No. 4,569,673 to Tesi. Tesi teaches placing a strip of an oligodynamic metal on a nonconductive substrate. The oligodynamic metal acts as a sacrificial galvanic anode and gives off ions when placed in conductive contact with a dissimilar metal by placing the catheter in an electrolytic solution. Because the conductivity and pH of urine, for example, varies over time within the same person, as well as from individual to individual, it would be extremely difficult to achieve a specific current density at a given time with any precision or predictability. Additionally, the Tesi device only provides localized infection control.

Thus, none of these devices fulfill the promise held out by oligodynamic iontophoresis for reducing infection in long-term indwelling medical devices.

SUMMARY OF THE INVENTION

The present invention provides an iontophoretic structure for a medical device that reduces the risk of infection associated with prolonged medical device implantation in the body. Specifically, the invention is directed toward meeting performance goals of general antibacterial effectiveness; minimal electrode corrosion; precise control of electrical current; portability of the current source; and ease of manufacture. These performance requirements can be readily addressed by a number of embodiments in which a controlled electrical current drives oligodynamic metal ions into solution to kill bacteria on and near the iontophoretic structure.

In one embodiment, an iontophoretic structure includes an iontophoretic material and a covering layer that covers at least a portion of the iontophoretic material. The covering layer can be chemically bonded, mechanically attached, or merged with the iontophoretic material. The iontophoretic structure can include an iontophoretic composite material, layered iontophoretic structures, or bodies overcoated with selected materials to create an iontophoretic effect.

The covering layer, which can be permeable, can include or comprise a hydrophilic substance, a blood thinner, or a non-iontophoretic polymer. In other embodiments, the iontophoretic structure further includes a coating covering at least a portion of the permeable covering layer. The coating can include a biodegradable material or a soluble material and a chemical or a biological agent that is liberated from the coating when the biodegradable material degrades or dissolves.

In another embodiment of the invention, an iontophoretic structure includes a permeable base material for a medical device that is integrated with iontophoretic bodies or structures.

In yet another embodiment of the invention, iontophoretic materials are provided as pellets containing or coated with two dissimilar galvanic metals and, optionally, a carbon-containing material. The materials may alternatively be provided,as carbon fibers coated with one or more galvanic metals.

DESCRIPTION OF THE DRAWINGS

The invention will be more fully understood from the following detailed description taken in conjunction with the accompanying drawings in which.

DETAILED DESCRIPTION OF THE INVENTION

Iontophoretic structures in accordance with the invention may be divided into two categories: a composite material used to coat a medical device, or a plurality of discrete layered electrodes placed on the medical device, both of which categories are disclosed hereinbelow. The medical device can be a short-term, long-term, or permanent implant and includes such devices as: urinary catheters, vascular access catheters and introducer sheaths, fluid introduction tubing and fittings such as intra-venous tubing, urinary drainage bags and tubing, chest drainage tubes, infusion pumps, pacing leads, tracheotomy tubes, ventilation tubes, prosthetic joints, heart valves, wound dressings, orthopedic pins or plates, or any other medical device used in an environment or application where anti-bacterial properties are a consideration. However, because urinary catheters are an especially attractive application for the iontophoretic structures, the ensuing detailed description is directed thereto.

Figure 1:
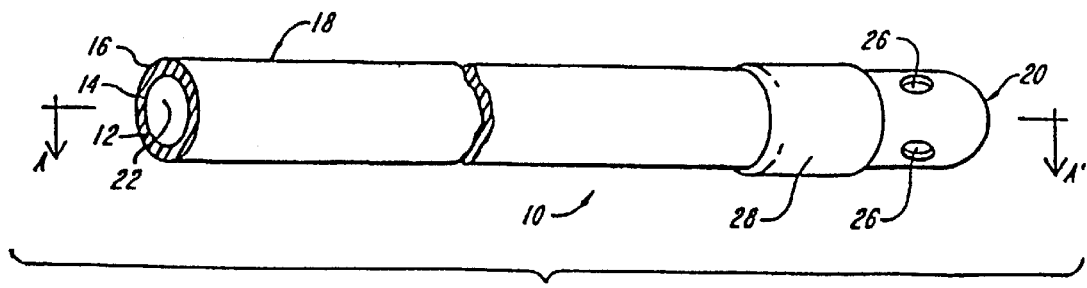
FIG. 1 is a perspective view of an iontophoresis catheter incorporating a composite material comprising metal powders in a conductive elastomeric matrix.

With respect to the first category of iontophoretic structure for a medical device, FIG. 1 illustrates an exemplary iontophoresis catheter 10 that uses the composite material approach to kill bacteria. The iontophoresis catheter 10 is substantially identical to a normal or non-infection controlling catheter in that it is a hollow flexible tube comprising an elastomeric wall 12 having an inner surface 14 and an outer surface 16, a proximal end 18, and a distal end 20. The generally cylindrical inner surface 14 defines a lumen 22 for the passage of fluid. Both the proximal end 18 and the distal end 20 are provided with one or more openings 26 to allow the fluid to be introduced or evacuated from the lumen 22. The distal end 20 is shaped to facilitate insertion or placement of the iontophoresis catheter 10 into the body. The iontophoresis catheter 10 may also be fitted with a retention device 28, such as a balloon fitting, to prevent unintentional withdrawal of the iontophoresis catheter 10 from the body.

Figure 2:
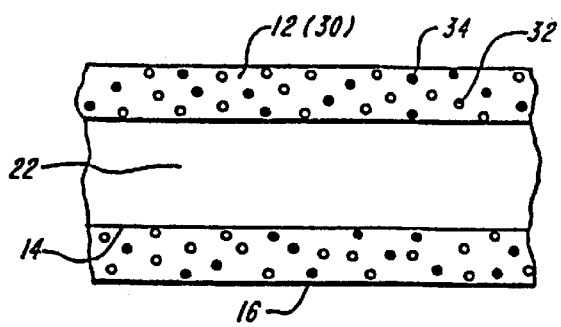
FIG. 2 is a partial sectional view of the iontophoresis catheter of FIG. 1.

FIG. 2 is a partial sectional view of the iontophoresis catheter 10 of FIG. 1, taken along the line A–A', that depicts details of a composite material comprising galvanic materials, such as metal powders, in a conductive elastomeric matrix 30 that distinguishes the iontophoresis catheter 10 from prior art catheters. The wall 12 of the catheter comprises the conductive base material 30, and a first and a second dissimilar metal powder, 32 and 34 respectively. The base material 30 is a conductive polymer similar to that used in static-proof bags for packaging charge-sensitive electronics in which the conductivity (resistivity) is controlled to a predetermined value by its composition. Exemplary conductive polymers can be made from polymers including polyvinyl, polyester, polyethylene, or aL naturally conductive polyvinylidene fluoride. When loaded with carbon or other conductive fillers, for example, these polymers can be made conductive and thereby used as the base material 30 for an iontophoresis catheter 10. Exemplary first and second metal powder combinations having an electrochemical half-cell potential difference include silver and gold, silver and copper, or silver and platinum mixed into the polymer at very low volume concentrations prior to extrusion fabrication of the composite catheter 10. Although these exemplary powders are relatively expensive, they are used in such minute quantities that their use does not adversely impact overall cost of the iontophoresis catheter 10.

For catheter applications in which the elastomeric wall 12 is extruded, it is feasible to make the entire wall 12 from the composite material 30, 32, 34. However, Foley catheters which are typically made of latex and/or silicone rubber are not extruded, but are generally dip-cast, and finish-coating in a final dip is a natural processing step in their manufacture.

Therefore, the iontophoresis catheter 10 can be made by finish-coating it with the composite material 30, 32, 34. Since rubber is generally inferior to plastic in terms of infection rates, overcoating with a castable plastic is advantageous in and of itself.

When the composite catheter 10 is placed in contact with or immersed in a fluid that is electrolytic, such as saline, blood, drug preparations, or urine, the first and second metal powders 32, 34 become an array of small batteries. Specifically, each powdered metal granule embedded in the base material 30 that makes contact with the electrolytic fluid 24 becomes either an anode or a cathode, depending on the particular metals chosen as the first and second metal powders 32, 34.

Figure 3:
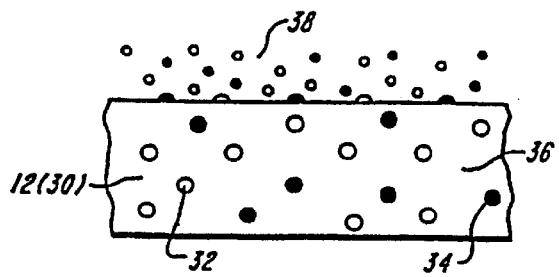
FIG. 3 is a depiction of the iontophoresis effect created by the composite material in the catheter of FIG. 1.

Referring to FIG. 3, a depiction of the iontophoresis effect created by the composite material 30, 32, 34 in the catheter of FIG. 2 is shown. The first and second metal powders 32, 34 act as electrodes and create a voltage potential therebetween, whereby electrons 36 migrate through the base material 30 and generate an electric current. Metal ions 38 are thus driven into the conductive fluid 24 by iontophoresis. The electric current is regulated by the quantity and nature of metal powder 32, 34 embedded in the base material 30 and by the conductivity of the base material 30. These factors are adjusted so that the current and ultimate metal ion densities are in an efficacious and safe range by use of the following formula:

$$I\left(\frac{AMP}{CM^2}\right) = \frac{V}{4r\rho} \ln\left[\frac{L^{-2/3}}{L^{-2/3}-1}\right]$$

wherein:
"I" is the total average current per unit surface area (amperes per $cm^2$)
"p" is the volume resistivity of the conductive base material 30 (ohm-cm);
"r" is the average metal powder granule radius (cm);
"V" is the voltage produced by the two dissimilar metals powders 32, 34 in the electrolytic fluid; and
"L" is the metal powder volume loading of the base material as a fraction (i.e. 0–1).

With respect to the above formula, the metal powders are assumed to be of the same granule size and of the same volume loading. In practice, they do not have to be the same size and volume loading. To achieve a current density between $10^{-8}$ to $10^{-6}$ Amperes per $mm^2$, which is the desired range to be bacteriostatic or bactericidal and yet not be so high as to cause pH changes or other deleterious mammalian cell reactions, the following exemplary values can be used in the above equation to define the composite material specifications:
V=0.12 volts (for silver and gold in an NaCl electrolyte);
r=$10^{-3}$ cm;
p=$1.5 \times 10^6$ to $1.5 \times 10^4$ ohm-cm; and
L=0.01.

An iontophoresis catheter 10 incorporating the above described composite material has numerous advantages over the prior art with respect to effectiveness, controllability, and ease of use. Foremost, bacterial potency is maximized because metal is guaranteed to go into solution as ions, thus producing a minimum ten-fold reduction in bacterial colonization rate.

Also, the iontophoresis catheter 10 does not need an external current source or controller because the iontophoresis current is self-generating and self-regulating. Furthermore, because the metal powders 32, 34 (electrodes) are dispersed through the base material 30, and because the current level is very low, the electrodes are functional for months of use. There is also no place in the circuit where corrosion of the electrodes at the air/electrolyte interface can cause the entire catheter to become non-functional with regard to its infection resistance. Finally, there is no change in procedure for placing or maintaining the iontophoresis catheter 10 because it is in many ways virtually identical to existing non-infection control devices in size and shape.

Figure 4:
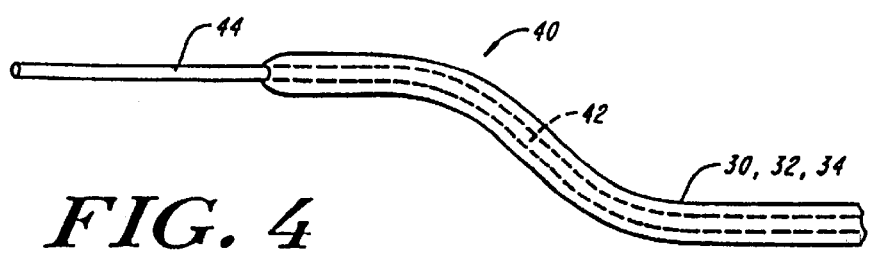
FIG. 4 is a perspective view of a pacing lead coated with the composite material of FIG. 1.
Figure 5:
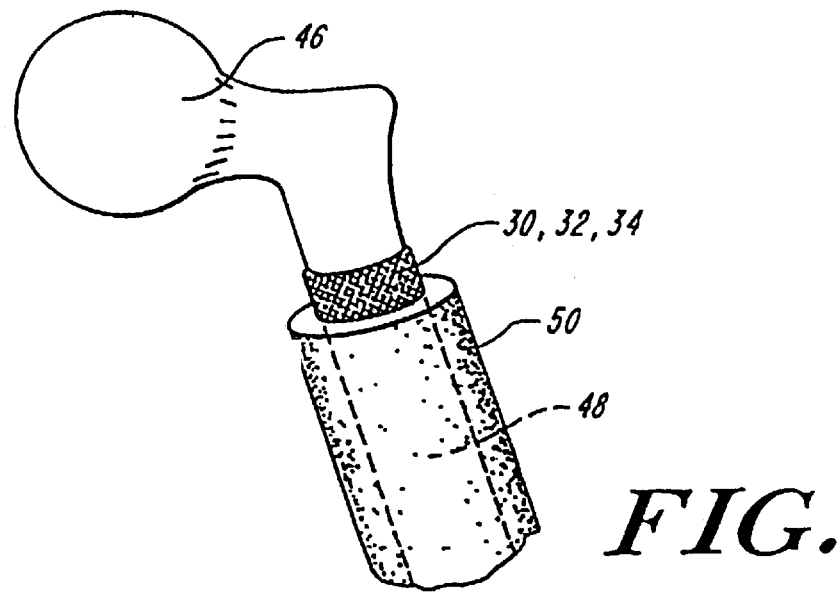
FIG. 5 is a perspective view of an artificial hip joint partially coated with the composite material of FIG. 1.
Figure 6A:
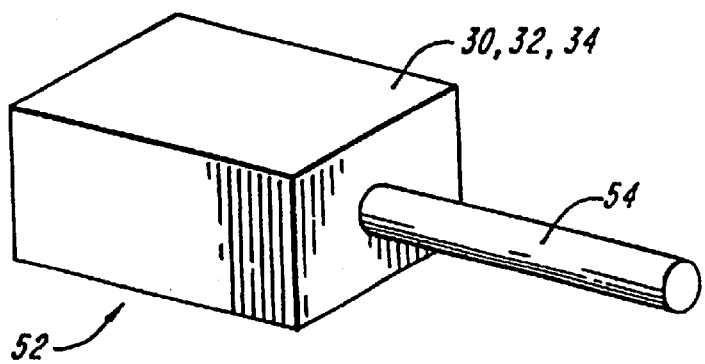
FIG. 6A is a perspective view of an infusion pump coated with the composite material of FIG. 1.

As previously discussed, the composite material approach finds ready application on numerous other medical devices where antibacterial properties are desirable. FIG. 4 is an illustration of the composite material 30, 32, 34 used to protect a pacing lead 40. The pacing lead 40 connects the heart tissue to the control and monitoring apparatus of a cardiac pacemaker (not shown) via a wire 42 and an electrode 44 in the tissue. The wire 42 is shown covered with the composite material 30, 32, 34. FIG. 5 is a depiction of the composite material 30, 32, 34 used with a prosthetic device, such as an artificial hip joint 46. The shaft 48 is shown coated with composite material 30, 32, 34 and implanted into a femur 50. FIG. 6A shows an infusion pump 52 coated with the composite material 30, 32, 34 and connected to tubing 54 which may also be coated.

Figure 6B:
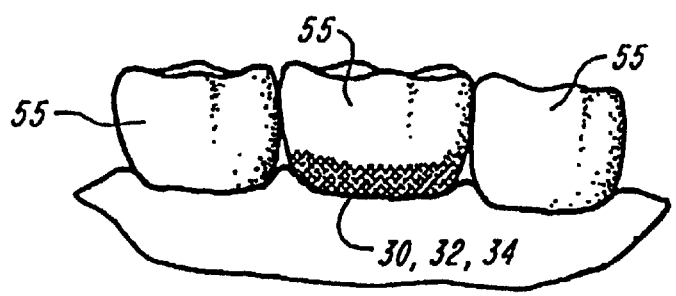
FIG. 6B is a perspective view of a tooth coated with the composite material of FIG. 1.

The composite material 30, 32, 34 can also be coated onto a natural body structure 55, such as a tooth, as illustrated in FIG. 6B. This is accomplished by painting the composite material 30, 32, 34 onto the surface to be protected while the base material 30 is in a liquefied or softened state and then letting the base material 30 harden. In an alternative embodiment the base material 30 is binary adhesive, such as a catalytic, two-part, conductive epoxy mix.

Figure 7:
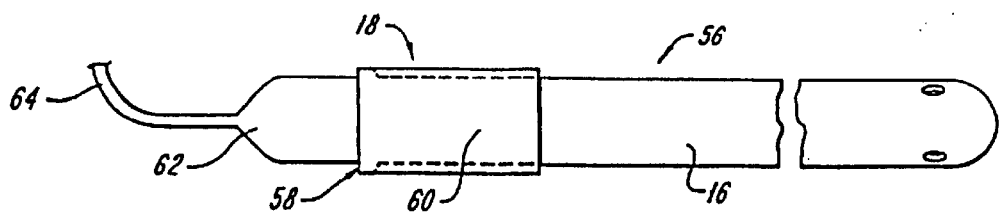
FIG. 7 is a perspective view of a catheter with an iontophoresis infection control sheath.

With further regard to catheters, a vascular access add-on device that benefits from the composite material approach for an iontophoretic structure is shown in FIG. 7, wherein an ordinary catheter 56 is shown fitted with an infection control kit 58 incorporating the composite material 30, 32, 34. The infection control kit 58 is an after-market device which includes a replaceable iontophoretic infection control sleeve 60 and an iontophoretic Luer adaptor 62 for connecting the proximal end 18 of the catheter 56 to intravenous (I.V.) tubing 64. The sleeve 60, made of or coated with the composite material 30, 32, 34 slips over the outer surface 16 of the catheter 56 to be inserted the body. The sleeve 60 covers only a short section of the catheter 56 near its proximal end 18, but is long enough to enter the body wherein moisture will activate the iontophoresis process. The sleeve 60 thus protects the catheter surface 16 from infection. The Luer adaptor 62 may also be made of or coated on the inner surface with the composite material 30, 32, 34 to protect the inner surface 14 of the catheter 56 from bacterial colonization progressing down to the catheter 56 from the inside of the I.V. tube 64. The sleeve 60 is fabricated from one of the above referenced conductive base materials 30; and the Luer adaptor 62 is made of a harder plastic, such as acrylic or polycarbonate. The sleeve 60 may be configured to accommodate a variety of catheter sizes.

Figure 8:
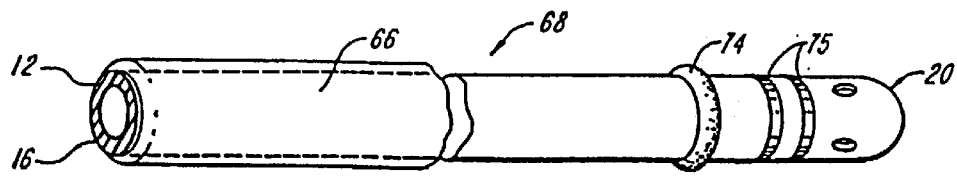
FIG. 8 is a perspective view of a catheter with an iontophoresis infection control introducer sheath.

An adaptation of the composite material sleeve 60 can also be configured as a catheter introducer sheath 66, shown in FIG. 8, for inserting pulmonary artery (Swan-Ganz or thermodilution) catheters, temporary pacing leads, etc., which may remain in place for several weeks. Under normal circumstances, an introducer sheath is left in place with the catheter which it surrounds for a portion of its length, including the region where the device penetrates the skin. Iontophoretic introducer sheaths 66 are easily manufactured with the composite material approach because they are predominantly made of polytetrafluoroethylene (Teflon®), vinyl (PVC), or polyethylene (PE), materials which can be loaded with carbon or other conductive fillers or made conductive by other means known in the art and then loaded as well as the first and second metal powders 32, 34.

FIG. 8 shows the introducer sheath 66 used in conjunction with a thermodilution catheter 68. Balloon and temperature sensing elements, 74 and 75 respectively, known to those skilled in the art, are shown on the distal end 20. Because the inside of the introducer sheath 66 is in intimate contact with the outer surface 16 of the elastomeric wall 12, the composite material 30, 32, 34 of the introducer sheath 66 protects both the sheath 66 and the outer wall 12 of the thermodilution catheter 68. Like the iontophoresis catheter 10, and the catheter 56 having an iontophoresis infection control kit 58, the introducer sheath 66 is virtually identical in size, shape, and use as prior art devices.

As described with respect to FIGS. 1–8, various embodiments of the composite material category of the iontophoretic structure for a medical device have been illustrated. In composite material embodiments, the integral power source for driving oligodynamic metal ions into solution is the electromotive force created by dissimilar metal powders 32, 34 embedded in and separated from each other by the conductive base material 30 of specifically created resistivity.

Figure 9:
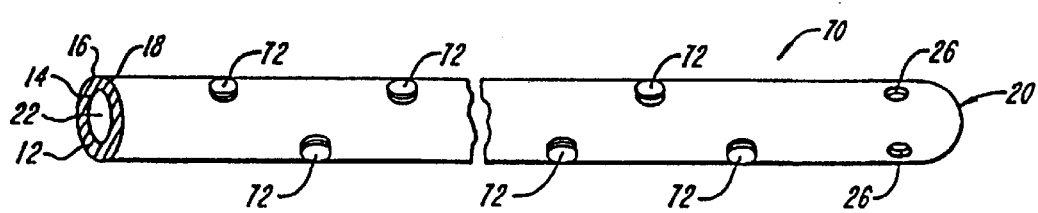
FIG. 9 is a perspective view of an iontophoresis catheter having a plurality of layered electrodes.
Figure 10:
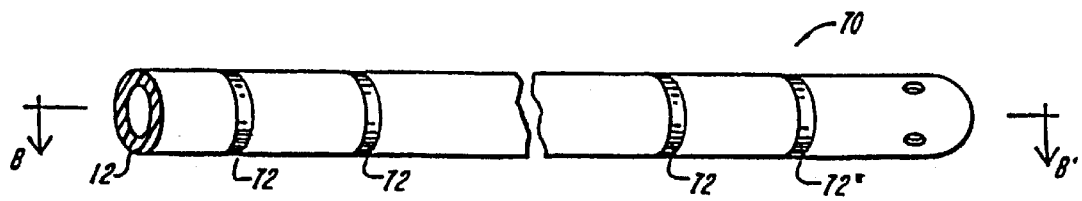
FIG. 10 is a perspective view of an alternative embodiment of an iontophoresis catheter having a plurality of layered electrodes arranged in strips.
Figure 11:
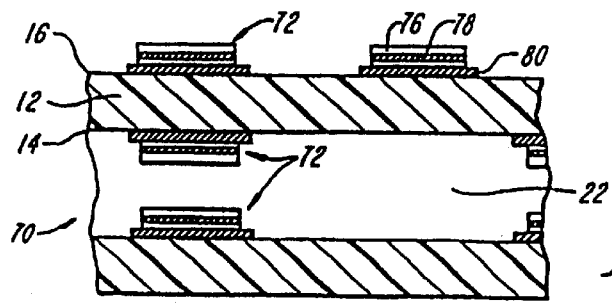
FIG. 11 is a partial sectional view of the iontophoresis catheter of FIG. 10.

Referring now to FIGS. 9–11, a variety of embodiments of the other category of iontophoretic structure for a medical device are shown which incorporate the plurality of discrete layered structures. In these embodiments a plurality of layered structures comprise dissimilar galvanic materials separated by a resistive layer. These structures may be incorporated in the above-recited medical devices during manufacture, or adhered to the surface of the devices as an aftermarket item.

Referring to FIG. 9 a perspective view of an embodiment of an iontophoresis catheter 70 is shown, wherein the oligodynamic iontophoresis effect is achieved using a plurality of layered structures 72 on either the inner surface 14, the outer surface 16, or both of a non-conductive wall 12. The layered structures 72, while depicted in a circular configuration can be any shape, such as oval or square.

FIG. 10 depicts an alternative configuration of the iontophoresis catheter 70, wherein the plurality of layered structures 72 are bands that surround the wall 12. Alternatively, the layered structures 72 can be a plurality of longitudinal strips. The embodiments of FIGS. 9 and 10 permit selective placement of a layered structure 72 on an isolated region of the wall 12, or distribution of the layered structures 72 on the entire wall 12.

Referring to FIG. 11, a partial cross section of the iontophoresis catheter 70 of FIG. 10 along the line B–B' is shown, wherein the layered structures 72 are bands adhered to the inner surface 14 and outer surface 16 of the wall 12. Each layered electrode 72 comprises a first metal electrode 76, a resistive layer 78, and a second metal electrode 80. As with the iontophoresis catheter 10 of FIG. 1, the metals are biocompatible and form an electrical potential difference between them in an electrolytic fluid. Whereas, in the iontophoresis catheter 10 of FIG. 1 the conductive (resistive) base material 30 regulates the current flow between the first and second metals 32, 34, in this embodiment the (conductive) resistive layer 78 regulates the current flow between the dissimilar metals of the first and second electrodes 76, 80.

For the iontophoresis catheter 70 of FIGS. 9 and 10, wherein the first and second metal electrodes 76, 80 of the layered structures 72 have a 1 volt potential between them, a current density of $10^{-8}$ Amperes per mm$^2$ results if the thickness of the resistive layer 78 is approximately 10 micrometers and has a bulk conductivity of $10^{11}$ Ohm-cm and the exposed area of each of the electrodes 76, 80 in the layered structures 72 is the same. Typical combinations of metals used for the first and second metal electrodes 76, 80 generate between 0.1 to 2 Volts. Therefore, the thickness of the above described resistive layer 78 can be between 1 and 20 micrometers. Many other combinations of conductivity and thickness for the resistive layer 78 are possible to obtain the target current density.

Figure 12:
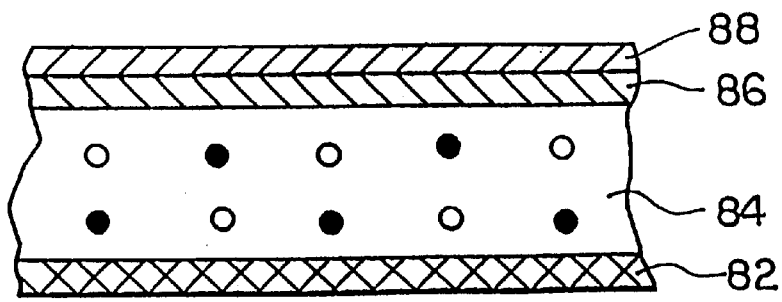
FIG. 12 is a sectional view of another embodiment of an iontophoretic structure on a device surface that includes one or more covering layers.
Figure 13:
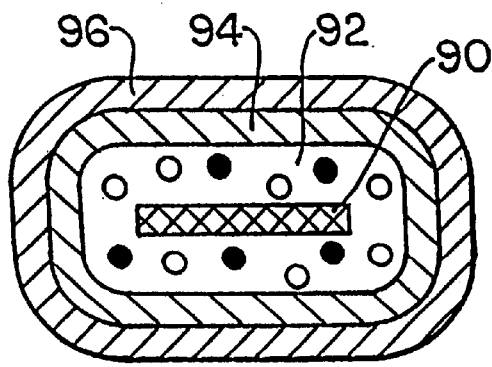
FIG. 13 is a sectional view of an iontophoretic structure that envelops a device and is itself enveloped by one or more covering layers.
Figure 14:
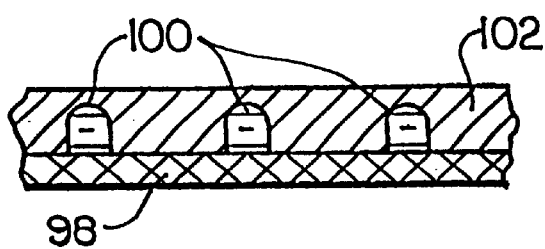
FIG. 14 is a sectional view of yet another embodiment of an iontophoretic structure on a device surface that includes a covering layer.

Although the above described iontophoretic structures and materials provide antibacterial and antifungal protection, certain configurations can be physically unstable or unsuitable for particular devices, and/or they may present an undesirable surface texture or finish for specific applications. The physical characteristics of devices incorporating or made from such structures or materials can be improved by providing them with a covering layer that stabilizes the structure and/or that provides a desired surface texture, finish, or other mechanical property. Even if the structure and properties of an iontophoretic structure or material are acceptable, it is sometimes desirable to provide supplemental benefits. As shown in FIGS. 12, 13, and 14, these goals can be accomplished in embodiments of the invention, wherein either all or a portion of an iontophoretic structure or composite material is provided with a permeable covering material that has different chemical, biological, mechanical, or physical properties from the underlying iontophoretic surface.

FIG. 12, for example, illustrates a substrate 82 that is representative of a surface portion of a medical device. The substrate 82 is covered with a material 84 that has iontophoretic properties. Although it is believed that when the material 84 includes an iontophoretic structure such as the composite material or the layered electrodes described hereinabove, a superior antibacterial effect is achieved, the material 84 can also include any other substance or structure known that creates an iontophoretic effect. Chemically bonded to, mechanically attached to, physically merged with, or merely covering an outer layer of the material 84 is a covering layer 86. The covering layer 86 is permeable or semi-permeable (collectively "permeable") to all of the ionic species necessary to cause the underlying iontophoretic material 84 to function. However, a non-permeable covering layer material that is either permanent or degradable can be applied to the iontophoretic material 84 to permanently or temporarily alter the iontophoretic effectiveness of the device across its entirety or at one or more localized regions.

The covering layer 86 can include a hydrophilic substance that improves lubricity or antithrombogenicity. The covering layer 86 can also include heparin for antithrombogenicity. To improve surface finish or to reduce the iontophoretic rate, the covering layer 86 can comprise a pure polymer. The covering layer can also comprise a different polymer from the iontophoretic materials for improved biocompatibility, or wear and fatigue properties. In an exemplary embodiment, a polyurethane based iontophoretic material is coated with silicone. In another embodiment, a silicone based iontophoretic material is coated with polyurethane.

Also as shown in FIG. 12, the covering layer 86 can be provided with a coating 88 that dissolves in its target environment or that is biodegradable to delay the onset of the iontophoretic action and/or to reduce the iontophoretic effect. Furthermore, the coating 88 can include chemicals or biologicals that provide other effects of interest and that are released when the coating dissolves or degrades. With respect to any of the materials selected for the covering layer 86 or the coating 88, a coloring agent or pigmentation can be added for aesthetic reasons and to identify device function or material properties.

The coating 88 can be provided, as shown in FIG. 12, as a layer that is separate and distinct from the permeable covering layer 86. Alternatively, the materials of the coating 88 and the covering layer 86 can be commingled to provide a single layer. In an exemplary embodiment a device is provided with a permeable, biodegradable layer or covering that has a lubricous surface for ease of placement of the device.

FIG. 13 illustrates yet another embodiment of an iontophoretic medical device, wherein a substrate 90 is completely enveloped by a material 92 that has iontophoretic properties as described above with respect to FIG. 12. Chemically bonded to, mechanically attached to, or physically merged with an outer layer of the material 92 is a covering layer 94, as described above with respect to FIG. 12, that completely envelops the material 92. The covering layer 94 can be provided with a coating 96 that dissolves in its target environment or that is biodegradable, as set forth above with respect to the coating 88 of FIG. 12. As set forth above, the covering layer 94 and the coating 96 can be one and the same layer.

FIG. 14 illustrates how the surface properties of a medical device including an iontophoretic structure or composite material can be improved when the medical device or the iontophoretic structure or material has an irregular, non-uniform, or rough surface, or comprises a number of discrete structures on the surface of a medical device. More specifically, FIG. 14 depicts a substrate 98, representative of the surface of a medical device, that is covered with layered structures 100, as shown with respect to FIGS. 9–11. The height of the layered structures 100 is exaggerated in FIG. 14 for illustrative purposes. A covering layer 102 is provided over the substrate 98 and the layered structures 100.

Figure 15:
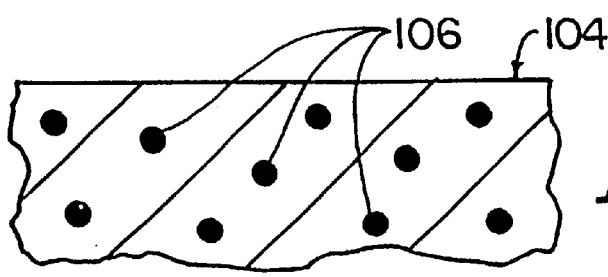
FIG. 15 illustrates a medical device that incorporates iontophoretic structures.

In addition to being partially coated or completely enveloped by iontophoretic material or structures, all or a portion of a medical device can be integrated with, impregnated by, or fabricated from an iontophoretic material. In some cases, it is desirable to leave a medical device base material in an unaltered state. In those cases, discrete iontophoretic structures can be incorporated as a composite into the base material as depicted in FIG. 15. More particularly, FIG. 15 illustrates a portion of a medical device 104 comprising a base material, wherein discrete iontophoretic structures 106 or material bodies are mixed with, dispersed through, or otherwise made integral with the base material of the medical device. The medical device 104, which can be of any shape or size, includes a base material that must be permeable or semi-permeable to the ion species necessary to cause the integral iontophoretic structure or material to function as described above. Although a medical device can be made entirely of the iontophoretic composite material, the configuration illustrated in FIG. 15 is intended for applications wherein the base material has certain desirable properties which one may wish to retain. It should be noted that the base material does not need to be conductive.

In an exemplary embodiment, particulates of an iontophoretic composite material or multiple layered structures, as described above, are embedded in a base polymer. In another embodiment, the iontophoretic material includes bodies made or coated with one of the dissimilar metals that are partially or completely overcoated with the second dissimilar metal, and the bodies are embedded in a base material. In yet another embodiment the iontophoretic material includes platinum bodies or platinum coated bodies that are partially or completely overcoated with silver and embedded in a base material. Alternatively, silver bodies or silver coated bodies that are partially or completely overcoated with platinum are embedded in a base material. The base material can be optically clear.

Figure 16:
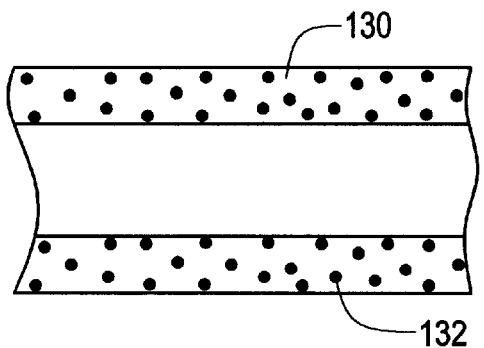
FIG. 16 is a partial sectional view of an iontophoretic matrix material in accordance with an alternate embodiment of the present invention.

Referring now to FIG. 16, a matrix 130 includes iontophoretic structures or materials 132 having a configuration different than the above-described configurations. The materials 132 are generally in pellet form and generally contain or are coated with two dissimilar, galvanic metals. Additionally, the pellets may be carbon-based and/or may contain or be coated with an electrically conductive, carbon-containing material.

Figure 17:
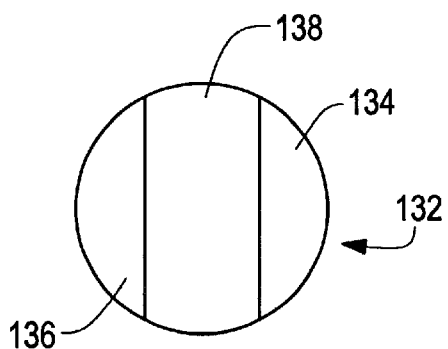
FIGS. 17–21 are cross-sectional views of different iontophoretic composite materials that may be dispersed on or throughout the matrix material of FIG. 16.
Figure 18:
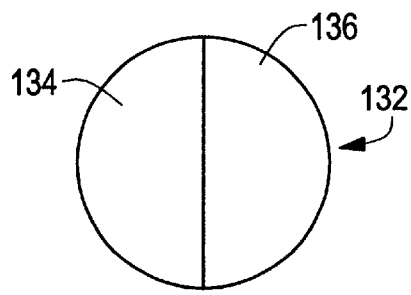
Figure 19:
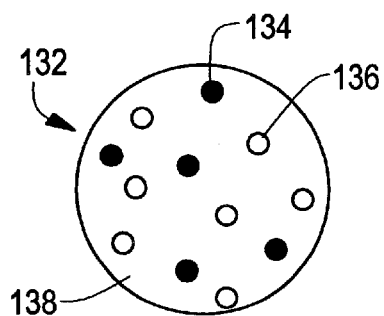
Figure 20:
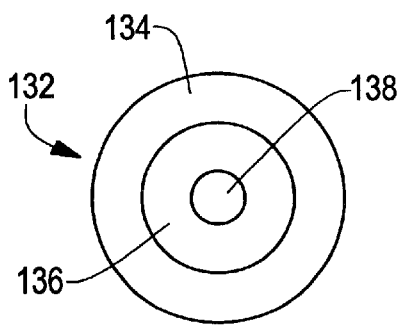

Exemplary configurations of pellets of the materials 132 are shown in FIGS. 17–21. FIG. 17 depicts a substrate or pellet 132 that has been coated with two dissimilar metals 134, 136. FIG. 18 depicts a pellet 132 wherein a substrate has been co-precipitated with two dissimilar metals 134, 136. FIG. 19 depicts a pellet 132 that has a plurality of particles or portions of two dissimilar metals 134, 136 distributed thereon. FIG. 20 depicts a layered pellet 132 wherein a substrate 138 has been coated in layers with two dissimilar metals 134, 136.

In FIGS. 17 and 19, the reference numeral 138 may represent either a non-coated portion of a conductive substrate or pellet, or a portion of pellet or substrate that has been coated with a carbon-containing material.

Figure 21:
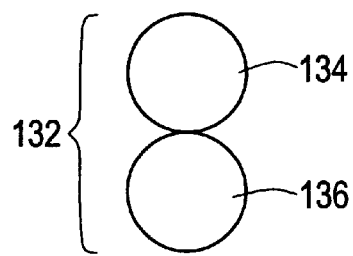

FIG. 21 depicts a pellet 132 that is formed of two or more conjoined, bound together, or otherwise connected pellets of two dissimilar metals 134, 136. Each of the sub-pellets that form the pellet 132 of FIG. 21 may itself be either a solid pellet of metal or a metal-coated, non-metal pellet. Furthermore, the term pellets, as used herein, is intended to indicate non-planar bodies including, but not limited to, grains, granules, chunks and powders. Pellets may have a smooth, edged or irregular surface and may be substantially spherical, substantially elliptical, substantially oblong or substantially ovaloid, among other shapes.

The matrix 130 shown in FIG. 16 may include any one, any several, or all of the types of pellets 132 that are depicted in FIGS. 17–21. Also, a matrix 130, such as that shown in FIG. 16, may include pellets that all have the same shape, pellets that all have a different shape, or some pellets that have the same shapes and some that have different shapes. Moreover, one of ordinary skill in the art will appreciate that the configurations of the pellets 132 depicted in FIGS. 17–21 and/or the ways in which the two dissimilar metals 134, 136 and/or the carbon-containing material 138 are placed on the pellets may be slightly varied in accordance with the present invention. Further, the material of the matrix 130 can be a conductive or non-conductive polymer as described above, or another flowable materi transitioned to a non-flowable state by drying, curing, etc., or a it can be a normally solid substrate or material.

The two dissimilar metals 134, 136 distributed throughout the pellets 132 function as electrodes when the pellets and/or a matrix 130 having the pellets distributed therein, thereupon or therethrough comes is contact with an electrolytic solution. Exemplary dissimilar metals 134, 136 that function as electrodes when they come into contact with an electrolytic solution include silver, gold, platinum and copper, with preferred combinations of the dissimilar metals being silver and gold, silver and platinum, or silver and copper. A matrix 130 may include pellets 132 having entirely identical combinations of dissimilar metals 134, 136 (i.e.—only silver and gold granules or only silver and platinum granules, etc.) or different combinations of dissimilar metals (i.e.—silver and gold granules as well as silver and copper granules throughout the matrix, etc.). Each of the pellets 132 are preferably embedded in, dispersed on, or otherwise placed on or throughout the matrix 130 such that they are separate from one another and in a generally uniform dispersion pattern. However, some irregularity in dispersion and some clumping (touching) is acceptable.

Figure 22:
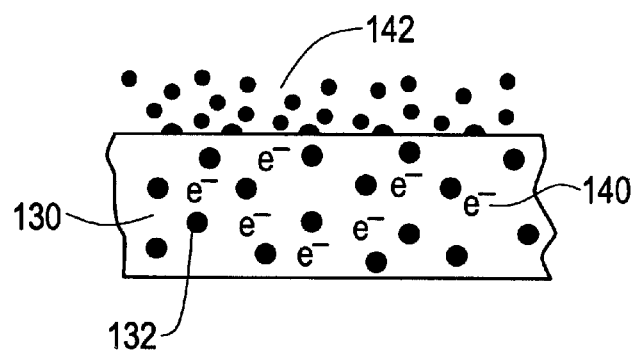
FIG. 22 is a depiction of the iontophoresis effect created by the materials dispersed on or throughout the matrix material of FIG. 16.

Referring now to FIG. 22, a depiction of an iontophoresis effect created by the matrix 130 and the pellets 132 is shown. Upon the contacting of an electrolytic fluid or solution (not shown) such as saline, blood, drug preparations, or urine, with the matrix 130, the dissimilar metal powders or granules 134, 136 distributed throughout the pellets 132 act as electrodes and create a voltage potential therebetween, whereby electrons 140 migrate through the pellets and, if the matrix is conductive, through the matrix, and metal ions 142 are driven into the electrolytic fluid. An internal electric current is created by the pellets and the electrolytic solution; the electric current is regulated by the quantity and nature of the dissimilar metals 134, 136 distributed throughout the pellets 132, and by the conductivity of the matrix 130. These factors are adjusted so that the current and ultimate metal ion densities are in an efficacious and safe range through the usage of the formula herein described with respect to FIG. 3 wherein the same exemplary values may be used to define the material specifications.

A device, e.g., a catheter, incorporating the above described antimicrobial, iontophoretic material(s) has numerous advantages over prior art devices without iontophoretic materials with respect to effectiveness, controllability, and ease of use. Foremost, bacterial potency is maximized because metal is guaranteed to go into solution as ions, which is the oligodynamic form of the metals. Second, only a minimum amount of loading of the matrix 130 with pellets 132 is required since each pellet in and of itself releases oligodynamic metal ions.

Figure 23:
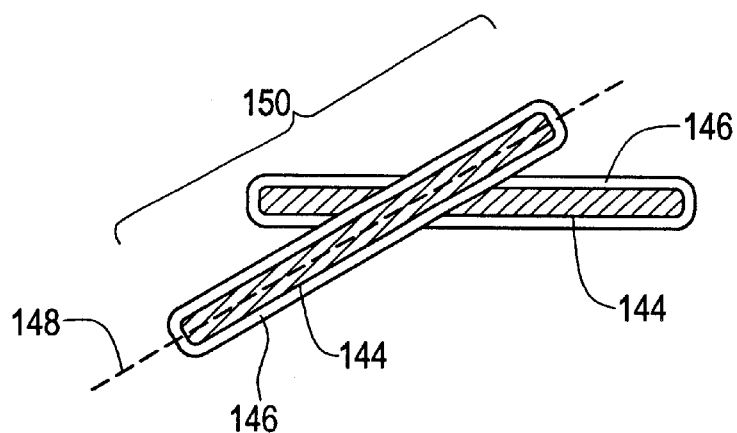
FIG. 23 is a perspective view of carbon fibers that are dispersed on or throughout the matrix material of FIG. 16 in an alternate embodiment of the present invention.

In yet another embodiment of the present invention, as depicted in FIG. 23, a conductive matrix material 132 includes a plurality of carbon or carbon-containing fibers 144 that have a galvanic electrical potential, have a conductivity, and are coated with at least one metal 146. When more than one metal is used to coat one or more of the carbon fibers, the metals should be dissimilar. Although the fibers 144 depicted in FIG. 23 are entirely coated with metal(s) 146, the fibers may also be partially coated with metal(s). Suitable metals 146 for coating the carbon fibers 144 include, but are not limited to, silver, gold, platinum, and copper.

Some examples of suitable shapes for the fibers 144 include, but are not limited to, substantially cylindrical, substantially oval, substantially round, substantially elliptical, and substantially helical. Generally, the fibers 144 will be substantially cylindrical, such as those shown in FIG. 18, and will have a longitudinal axis 148 and a longitudinal length 150 that is between about one micrometer and about fifty micrometers. Also, the fibers 144 may be oriented randomly on or throughout the matrix material, but should in such concentration such that each fiber is touching at least one other fiber. One of ordinary skill in the art will, however, appreciate that the geometry of the carbon fibers 144 and/or the orientation of the carbon fibers may be varied from the above examples.

In general, with respect to FIGS. 16 and 22, if the matrix is non-conductive, then pellets/fibers that are coated with two dissimilar metals do not have to be in contact with each other; however, pellets/fibers that are coated with only one metal must be in contact. But, if the matrix is conductive, electrical contact is achieved through the matrix, and thus the pellets/fibers do not need to be in physical contact with each other, regardless of whether or not they contain one or more metals or metal coatings.

Although the invention has been shown and described with respect to exemplary embodiments thereof, various other changes, omissions and additions in form and detail thereof may be made therein without departing from the spirit and scope of the invention.

What is claimed is:

1. An iontophoretic catheter or fluid introduction tube, said iontophoretic catheter or fluid introduction tube comprising an antimicrobial material comprising:

a matrix material;

a plurality of pellets distributed throughout the matrix material;

a first galvanic material distributed on each of the pellets; and a second galvanic material distributed on each of the pellets.

2. An antimicrobial material comprising:

a matrix material;

a plurality of pellets distributed throughout the matrix material;

a first galvanic material distributed on each of the pellets;

a second galvanic material distributed on each of the pellets; and a carbon-containing material distributed on at least some of the pellets.

3. An antimicrobial material comprising:

a matrix material;

a plurality of pellets distributed throughout the matrix material;

a first galvanic material distributed on each of the pellets; and a second galvanic material distributed on each of the pellets, wherein at least one of the plurality of pellets has quantities of the first and second galvanic material distributed thereon such that the first and second galvanic material are not in contact.

4. An antimicrobial material comprising:

a matrix material;

a plurality of pellets distributed throughout the matrix material;

a first galvanic material distributed on each of the pellets;

a second galvanic material distributed on each of the pellets; and a second galvanic material distributed on each of the pellets, wherein at least one of the plurality of pellets has quantities of the first and second galvanic material distributed thereon such that the first and second galvanic material are in contact, wherein at least one of the plurality of pellets has one of the first and second galvanic material distributed thereon and the other of the first and second galvanic material is distributed on the one of the first and second galvanic material.

5. An antimicrobial material comprising:

a matrix material;

a plurality of pellets distributed throughout the matrix material;

a first galvanic material distributed on each of the pellets;

a second galvanic material distributed on each of the pellets; and the first galvanic material and the second galvanic material are each metals selected from the group consisting of silver, gold, platinum and copper.

6. The antimicrobial material of claim 5, wherein at least one of the first and second galvanic material is distributed on each of at least some of the plurality of pellets by coating.

7. The antimicrobial material of claim 5, wherein at least one of the first and second galvanic material is distributed on each of at least some of the plurality of pellets by co-precipitation.

8. The antimicrobial material of claim 5, wherein at least one of the plurality of pellets is carbon-based.

9. The antimicrobial material of claim 5, wherein at least one of the plurality of pellets has quantities of first and second galvanic material distributed thereon such that the first and second galvanic material are in contact.

10. The antimicrobial material of claim 9, wherein at least one of the plurality of pellets is comprised of at least two attached pellets, each of the attached pellets having one of the first and second material distributed thereon.

* * * * *